(12) United States Patent
Wu et al.

(10) Patent No.: US 7,821,622 B2
(45) Date of Patent: Oct. 26, 2010

(54) OPTICAL REFRACTOMETER FOR MEASURING SEAWATER SALINITY AND CORRESPONDING SALINITY SENSOR

(75) Inventors: Zong Yan Wu, Brest (FR); Jean-Louis De Dougrenet De La Tocnaye, Guilers (FR); Marc Le Menn, Plouvien (FR); Philippe Grosso, Lannion (FR)

(73) Assignee: GET/ENST Betagne, Brest (FR)

( * ) Notice: Subject to any disclaimer, the term of this patent is extended or adjusted under 35 U.S.C. 154(b) by 127 days.

(21) Appl. No.: 11/996,828

(22) PCT Filed: Jul. 21, 2006

(86) PCT No.: PCT/EP2006/064492
§ 371 (c)(1),
(2), (4) Date: Jul. 28, 2008

(87) PCT Pub. No.: WO2007/012607
PCT Pub. Date: Feb. 1, 2007

(65) Prior Publication Data
US 2009/0122300 A1 May 14, 2009

(30) Foreign Application Priority Data
Jul. 26, 2005 (FR) .................................. 05 07996

(51) Int. Cl.
*G01N 21/41* (2006.01)
(52) U.S. Cl. .................................................... 356/128
(58) Field of Classification Search ................. 356/128, 356/517
See application file for complete search history.

(56) References Cited

U.S. PATENT DOCUMENTS

| 4,320,291 | A | | 3/1982 | Uramoto | 250/227 |
| 5,151,752 | A | * | 9/1992 | Oono et al. | 356/128 |
| 6,130,439 | A | * | 10/2000 | Le Menn | 250/573 |
| 6,484,562 | B2 | * | 11/2002 | Fabinski et al. | 73/31.05 |

FOREIGN PATENT DOCUMENTS

| EP | 0 289 833 | 11/1988 |
| EP | 0 598 968 | 1/1994 |
| EP | 0 598 968 | 6/1994 |
| GB | 2 074 316 | 10/1981 |

OTHER PUBLICATIONS

International Preliminary Report on Patentability from counterpart foreign Application No. PCT/EP2006/064492.
International Search Report from counterpart foreign Application No. PCT/EP2006/064492.
English Translation of International Search Report in counterpart foreign application No. PCT/EP2006/064492 filed Jul. 21, 2006.

* cited by examiner

Primary Examiner—Roy Punnoose
(74) Attorney, Agent, or Firm—David D. Brush; Westman, Champlin & Kelly, P.A.

(57) ABSTRACT

An optical refractometer is provided for measuring the refractive index of a liquid. Such a refractometer includes a first optical block having a transparent material whereto is secured a light source, a second optical block having a transparent material whereto is secured a position sensor. The optical blocks are arranged on either side of a conduit wherein the liquid flows.

22 Claims, 4 Drawing Sheets

OPTICAL REFRACTOMETER FOR MEASURING SEAWATER SALINITY AND CORRESPONDING SALINITY SENSOR

CROSS-REFERENCE TO RELATED APPLICATION

This Application is a Section 371 National Stage Application of International Application No. PCT/EP2006/064492 A1, filed Jul. 21, 2006 and published as WO 2007/012607 on Feb. 1, 2007, not in English.

FIELD OF THE DISCLOSURE

The field of the disclosure is that of the measurement of physical characteristics of liquids.

More precisely, the disclosure concerns the measurement of the refractive index of liquids, in particular sea water, in order for example to produce a salinity sensor meeting oceanographical requirements, for example for equipping immersed measuring probes.

BACKGROUND OF THE DISCLOSURE

The salinity of water is determined today essentially by a measurement of its electrical conductivity, at a known temperature and pressure. Conductivity sensors are however unreliable since they are very sensitive to degradation relating to the marine environment (as explained by the document "Capteurs de conductivité en océanographie: état de l'art et perspectives." ("Conductivity sensors in oceanography: state of the art and prospects") by M Le Menn, published in RSTD Vol. 64, pp 107-111, June 2004).

The use of other methods based on the measurement of the refractive index of sea water (as illustrated by the document "Remote refractive index difference meter for salinity sensor" by H Minato et al, published in IEEE Trans on Instrumentation and Measurements, Vol. 38, No 2, pp 608-612, 1989) or the use of fibre sensors can be envisaged.

Measurement of the index makes it possible, knowing the temperature and pressure, to find the salinity level either through the use of the equations of R. C. Millard and G. Seaver (R. C. Millard and G. Seaver, "An index of refraction algorithm for sea water over temperature, pressure, salinity, density and wavelength", Deep-Sea Research, Vol. 37, No 12, pp 1909-1926, 1990), the accuracy of which is 0.024 ppt in salinity, or by direct calibration for temperature, pressure and salinity. Which assumes that it is possible to measure the refractive index of sea water with a resolution of at least $10^{-6}$ in oceanographical ranges.

Having regard to the intended application, the salinity sensor must be compact and of low cost. The major problem is controlling the drift in measurement with respect to the variations in temperature and pressure that the device must undergo when it is used in situ. This point is all the more critical since the device is disposable, which confirms relative independence of the sensor and low cost. During uses for long periods in a marine environment, another problem has to be resolved: that of resistance to dirt or organic deposits of all kinds or fouling, which in general terms cause degradation of the measuring devices.

SUMMARY

An aspect of the present disclosure relates to an optical refractometer for measuring the refractive index of a liquid.

According to an embodiment of the invention, such a refractometer comprises a first optical unit consisting of a transparent material to which a light source is secured, a second optical unit consisting of a transparent material to which a position sensor is secured (in particular a high-resolution sensor), said optical units being disposed on each side of a conduit in which the liquid flows.

This refractometer is preferentially used as a high-resolution salinity sensor (the salinity of a liquid being able to be determined from the refractive index of the liquid).

Optical unit means a solid module that is produced from material that is transparent for the wavelengths in question (in the context of an embodiment of the present invention essentially in the near infrared, the visible range or the near ultraviolet).

Thus a quantity of liquid (for example sea water) enters and flows in the conduit, which enables the refractometer to determine the refractive index of this liquid and therefore to derive therefrom the salinity of this liquid.

This refractometer is distinguished from the refractometer of the aforementioned document of H Minato in particular through the fact that it makes it possible to measure the refractive index and in particular the salinity of a liquid in circulation by virtue of the use of a conduit.

Thus it is therefore not only adapted to make measurements in situ, and measurements at various depths or geographical situations (in particular in an ocean, a sea, a lake, etc.) but also limits the effects of fouling by virtue of its particular geometry. This is because a conduit with a cross section of approximately 1 cm is chosen for example, which avoids the effects of turbulence and makes it possible for example to fix TBT (tributyltin) pellets in the conduit, which has the effect of limiting the effects of fouling.

It also offers the possibility of controlling the thermal response time of the refractometer.

This is because the response time depends on the ratio between the length and diameter of the heat exchange surface between the liquid and the conduit as well as the rate of flow of the liquid. The use of a conduit makes it possible to fix the value of these two variables at will, the flow rate of the liquid also being able to made constant by the use of a pump.

The choice of a cross section of the conduit of 1 cm is a compromise between a cross section sufficient to allow good thermal conduction (between the liquid and the salinity sensor) but not too great to prevent turbulence.

Moreover, its novel inventive geometry based on two distinct optical units advantageously makes it possible to use simply, effectively and at low cost various ingenious characteristics (described below) in order to make it insensitive to the variations in temperature and pressure of the environment in which it is placed.

Preferentially the liquid is sea water and the refractometer is able to function when it is immersed.

According to an advantageous characteristic of an embodiment of the invention, the light source is a laser source cooperating with focusing means for focusing the laser beam onto the position sensor.

Advantageously, the size of the spot of the laser beam focused on the position sensor is between 200 Mm and 1 mm.

Thus it is possible to obtain, over this range of spot size, a resolution of the refractometer greater than $10^{-6}$.

Preferentially the focusing means are disposed close to the laser source.

According to an advantageous characteristic of an embodiment of the invention, the laser source emits in the visible range.

According to a first advantageous implementation of an embodiment of the invention, the first and second units are disposed close to each other and form a V for housing the conduit, the first unit comprises a first side comprising a first mirror and the second unit comprises a second side comprising a second mirror, so that the laser beam is reflected onto the first mirror, passes through the conduit and is reflected onto the second mirror.

Preferentially, the angle of refraction of the laser beam in the liquid in the conduit is between 29° and 31°.

Advantageously, the refractometer according to an embodiment of the invention comprises return means for holding the conduit against the V.

According to a second advantageous implementation of an embodiment of the invention, the first and second optical units are substantially aligned on each side of the conduit.

According to a first embodiment of the invention in accordance with the aforementioned instrumentation, the cross section of the conduit is substantially circular at the point where the laser beam passes through it and first and second windows are provided respectively between the first unit and the conduit and between the conduit and the second unit.

Thus the use of transparent windows makes it possible to make the interfaces between the first optical unit and the liquid and the liquid and the second optical unit planar, which avoids the effects of broadening of the laser beam resulting from curved interfaces (or dioptres).

Preferentially, the cross section of the conduit is substantially polygonal at the point where the laser beam passes through it.

According to a second embodiment of the invention in accordance with the aforementioned first implementation, the cross section of the conduit is substantially hexagonal at the point where the laser beam passes through it.

According to a third embodiment of the invention in accordance with the aforementioned first implementation, the cross section of the conduit is substantially prismatic at the point where the laser beam passes through it.

Thus, according to these three embodiments, the shape of the cross section of the conduit and the geometry of the two optical units of the refractometer make negligible the movements of the laser beam spot on the position sensor due to the variations in pressure in the conduit.

Advantageously, the transparent material or materials are chosen from all the materials comprising:

N-K5
N-F2
N-BAF51
N-LF5
N-SF5
N-SK10

These materials have a very low thermo-optical coefficient, around $10^{-7}$ $K^{-1}$. This makes it possible to obtain good-quality resolutions without having to use a system for compensating for the shifts in the laser beam spot with the respect to the position sensor due to variations in the indices of the optical units as a function of temperature.

According to a first advantageous solution of the invention, the first and second units are produced respectively from first and second transparent materials, the first and second materials having thermo-optical coefficients that are opposite and substantially equal in absolute value.

This first solution makes the optical path travelled by the laser beam insensitive to variations in temperature. This is because the variations as a function of temperature in the optical path followed by the laser beam in the first unit are compensated for by the variations as a function of temperature in the optical path followed by the laser beam in the second unit. In this way a compensation for the shifts of the laser beam spot with respect to the position sensor due to the variations in the optical path travelled in the optical units as a function of temperature is achieved.

This first technique for compensating for the effects of the variations in temperature makes it possible to produce salinity sensors at low cost.

Advantageously, the first and second materials are respectively N-BK7 and N-LLF1 or N-K5 and N-SK10.

Preferentially, at least one of the first and second units is at least partially hollowed out, the hollow or hollows being intended to receive thermally conductive materials in order to reduce the thermal inertia of said unit or units.

According to a second advantageous solution of the invention, the refractometer comprises a temperature sensor and electronic processing means in order to measure the variation in temperature of at least one of the optical units and to derive therefrom the salinity or the refractive index of the liquid.

Thus, by virtue of knowledge of the temperature of the optical unit, it is possible to make a compensation of a software nature (after obtaining measurements) for the shifts in the laser spot with respect to the position due to the variations in the index of the optical units as a function of temperature.

According to a third advantageous solution of the invention, the position sensor is secured to a support, the dimensions of which vary as a function of the temperature so as to compensate for at least one shift of the optical beam with respect to the position sensor as a function of temperature.

Thus an alternative is obtained to the aforementioned compensation based on materials having opposite thermo-optical coefficients and to the aforementioned software compensation for the shifts in the laser spot with respect to the position sensor resulting from the variation in the index of the optical units as a function of temperature. This alternative has the advantage of not having to carry out processing of the data measured.

According to a first advantageous characteristic, the support is produced from a thermally conductive material and at least part of the support is in thermal contact with the liquid to be measured.

According to a second advantageous characteristic, the support is produced from a thermally conductive material and the variation in its dimensions is slaved, by virtue of processing means, to at least one temperature sensor mounted close to at least one of said optical units.

An embodiment of the invention also concerns a salinity sensor comprising a refractometer as described previously.

BRIEF DESCRIPTION OF THE DRAWINGS

Other characteristics and advantages will emerge more clearly from a reading of the following description of a preferential embodiment, given by way of simple illustrative and non-limitative example, and the accompanying drawings, among which.

DETAILED DESCRIPTION OF ILLUSTRATIVE EMBODIMENTS

The general principle of an embodiment of the invention is based on a particular geometry of a refractometer used as a salinity sensor, using two optical units substantially symmetrical around a conduit and a high-resolution position sensor (for example a sensor of the PSD type, standing for "Position Sensing Detector") in order to obtain a precise measurement of salinity and which can easily be made insensitive to the pressure and temperature of the environment in which the refractometer is placed.

Thus an embodiment of the invention is based on two main characteristics:
 the mounting of the refractometer in itself makes it possible to obtain a maximum deviation of the refracted beam (and therefore good resolution), and insensitivity of the measurement to the variations in pressure of the liquid to be measured, and
 the use of a thermal compensation device that makes the refractometer itself insensitive to the effects of temperature.

These two characteristics are used cooperatively to guarantee low dependency on environmental variations at low cost and in a very compact manner. The principle of use adopted also makes it possible to adapt effective means for limiting the effects of fouling of marine origin and offers the possibility of controlling the thermal response time of the device.

Hereinafter the preferential context will be adopted of a use of the refractometer according to an embodiment of the invention for producing a sea water salinity sensor.

The geometry and dimensions of the various components of the refractometer, and in particular the conduit in which the sea water flows, comply with the three essential requirements mentioned below.

First of all, the refractometer must be able to measure any change in refractive index of the water, whether it be due to a change in pressure, temperature or salinity. The insensitivity to pressure and temperature signifies that, whatever the pressures and temperatures applied to the device, the latter must give the "true" value of the index of the liquid that it measures, and the problem therefore stems from the dependency on pressure and temperature of the indices of the materials used for producing the refractometer rather than from the dependency of the index of the liquid to be measured on pressure and temperature.

Next, in the case of a measurement of refractive index, the flow configuration must preferably be laminar rather than turbulent (which is preferred in the context of a conductivity sensor because turbulence affords better heat exchange). It is considered, having regard to the flow rates of the water in the conduit in the applicative context, that an effective cylinder or prism cross section of approximately 1 cm presents a good compromise between limitation of turbulence, flow effects and satisfactory thermal response.

Finally, the choice of transparent materials of the optical units is also determined by the thermal balance of the refractometer (or salinity sensor).

Figure 1A:
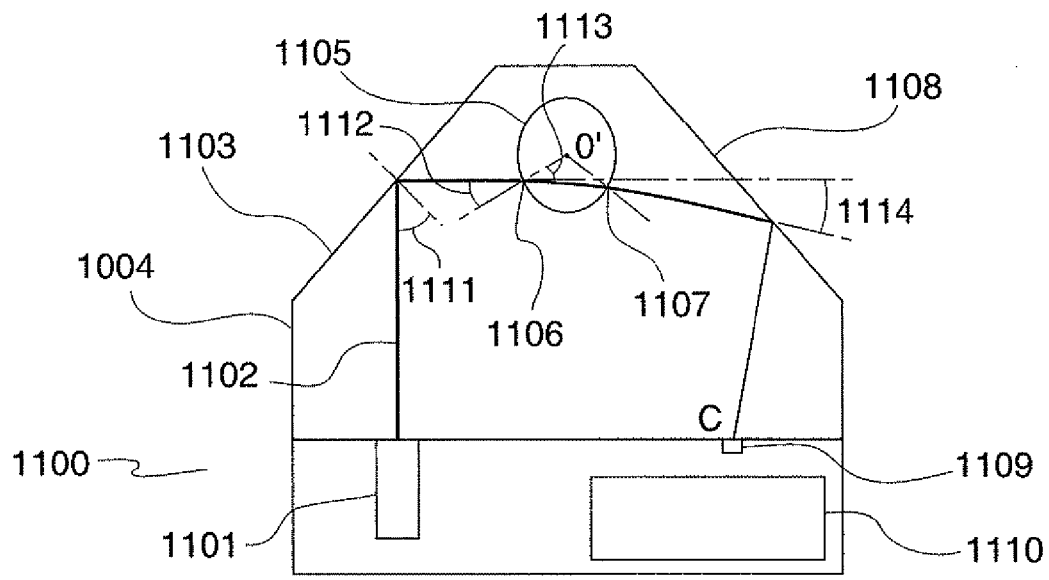
FIGS. 1A to 1C illustrate the operating principle of three types of refractometer according to a first implementation of the invention corresponding respectively to a first embodiment in which the cross section of the conduit is cylindrical (FIG. 1A), a second embodiment according to which the cross section of the conduit is hexagonal (FIG. 1B) and a third embodiment according to which the cross section of the conduit is prismatic (FIG. 1C)
Figure 1B:
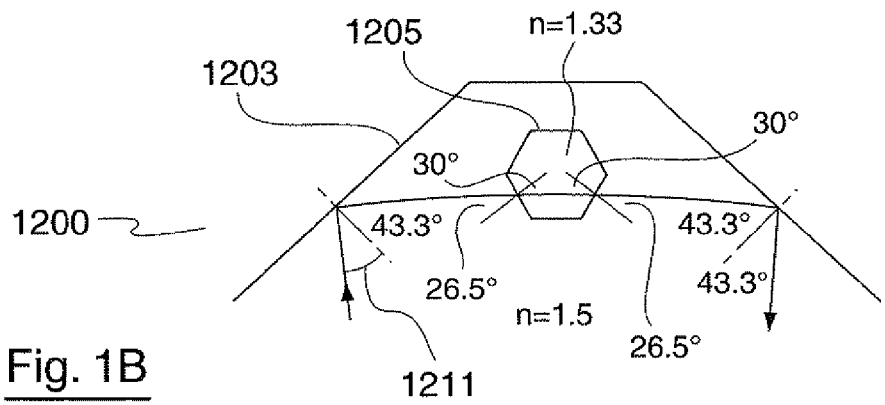
Figure 1C:
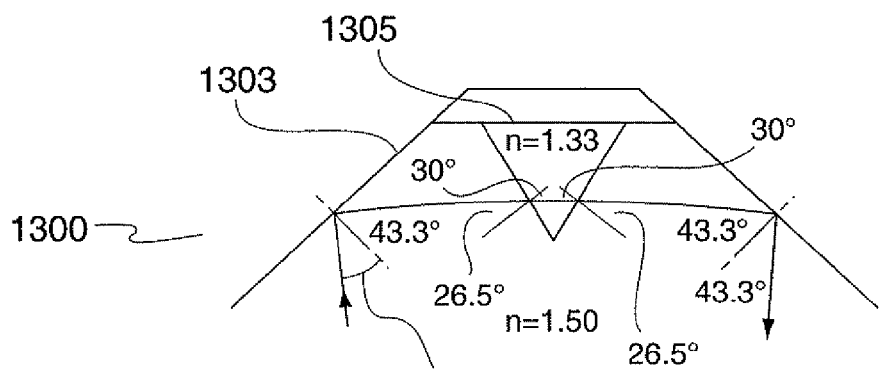

The operating principle of three types of refractometer according to a first implementation of the invention corresponding respectively to a first embodiment in which the cross section of the conduit is cylindrical (FIG. 1A), a second embodiment according to which the cross section of conduit is polygonal, for example hexagonal (FIG. 1B), and a third embodiment according to which the cross section of the conduit is prismatic (FIG. 1C) is illustrated in relation to FIGS. 1A to 1C.

Figure 5:
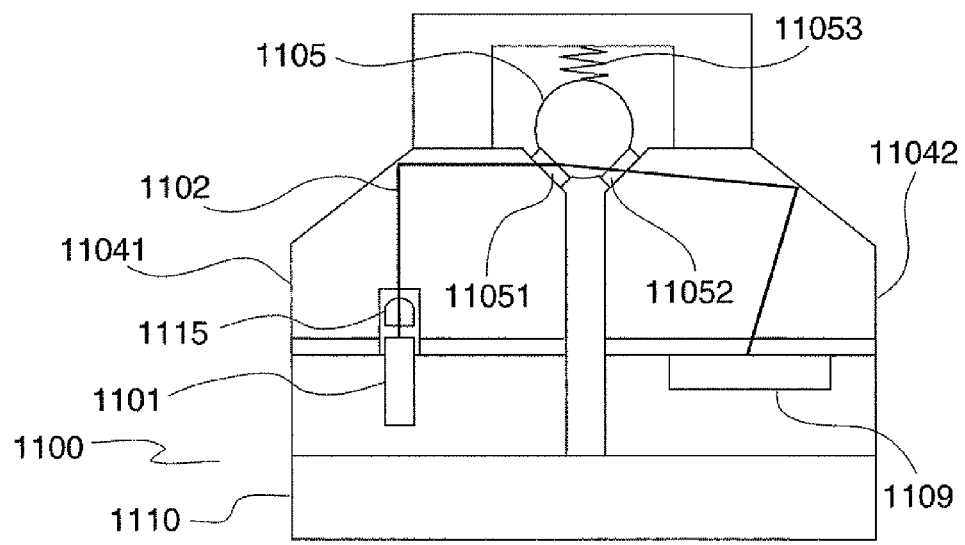
FIG. 5 presents a detailed diagram of the optical units of the refractometer according to the first embodiment of the invention.

These diagrams in FIGS. 1A to 1C are presented only to illustrate the operating principle of the refractometer according to a first implementation of the invention. Thus, for reasons of simplicity, the first and second optical units have been depicted in the form of a single global optical unit 1104 that must be considered to be formed by the first and second optical units (as illustrated by FIG. 5 described below).

The first refractometer 1100 according to the first embodiment of the invention comprises a light source that is for example a laser diode 1101 emitting in the visible range.

The laser diode 1101 emits a laser beam 1102 that is reflected on a first side 1103 (forming a mirror) of the global optical unit 1104 and then passes through the conduit 1105. After having passed through the conduit 1105, the beam 1102 is therefore diverted by refraction at the interface 1106 between the global optical unit and the sea water of the conduit 1105 and at the interface 1107 between the sea water and the global optical unit. The beam 1102 is then reflected on a second side 1108 (forming a mirror) of the global optical unit 1104 and is then detected by the position sensor 1109. An electronic unit 1110 processes the signals of the position sensor 1109 and derives the refractive index of the sea water as well as the salinity of the sea water.

The position sensor 1109 has a useful length of approximately 2 mm.

Focusing optics (not shown in this FIG. 1A), for example a lens, focuses the beam 1102 of the laser diode 1101 on the position sensor 1109 so as to obtain a focused beam with a spot diameter of approximately 200 Mm at the position sensor 1109.

Naturally other spot diameters can be chosen (preferentially a diameter of between 200 Mm and 1 mm) for the laser beam focused at the position sensor 1109 without departing from the scope of the present invention.

This is because, over this range of spot diameters, a resolution of the refractometer of greater than $10^{-6}$ is obtained.

The focusing optics can be disposed at the output of the laser beam, or at any point on the optical path of the laser beam 1102.

The laser beam 1102 forms an angle of incidence 1111 of substantially 450 on the first side 1103 and an angle of incidence 1112 of substantially 26.5° on the interface 1106 between the global optical unit and the conduit on the global unit side. Thus the angle of refraction 1113 on the conduit side is substantially 30°.

If the case is adopted of a global optical unit formed from glass with a refractive index of 1.5, the deviation 1114 of the beam generated by the refraction at the conduit 1105 is equal to substantially 8.394+1.450 when the refractive index of the sea water is between 1.31 and 1.36.

According to variants of the aforementioned first, second and third embodiments, the first 1103 and second 1108 sides can be covered by a mirror or any layer of material reinforcing the reflectivity, for example a layer of gold.

In the case of the refractometers 1200, 1300 of the second (conduit 1205 with a hexagonal cross section) and third (conduit 1305 with a prismatic cross section) embodiments of the invention, the angle of incidence 1211, 1311 formed by the laser beam at the first side 1203, 1303 is substantially 43.3°.

For reasons of simplicity, the laser, the focusing optics or the position sensor have not been shown in FIGS. 1B and 1C.

The aforementioned refractometers 1100, 1200, 1300 are equivalent from the point of view of the geometric optics and allow maximum deviation of the refracted beam. The angle of incidence on the first side (45° or 43.3° according to the case) preserves a constant angle of incidence in both cases with respect to the normal to the global optical unit/sea water dioptre of the conduit.

The secondary effect of field curvature caused by the assembly must nevertheless be considered.

In the context of the refractometers 1200, 1300 (conduits with a hexagonal or prismatic cross section) according to the aforementioned second and third embodiments, if a mean index for the sea water of 1.33 is taken into account, there is no effect of broadening of the beam.

For a refractive index of the sea water varying between 1.31 and 1.35, the angle of refraction varies by +0.89°, and therefore the diameter of the laser beam (for a mean angle of refraction on the conduit side of 30°) varies in the ratio of the cosines (cos (30−0.89)/cos (30+0.89)=1.02) that is to say by +1% without changing the deviation angles. However, the position sensor makes a correct measurement of the deviation with a beam whose diameter varies by 198 to 202 μm, and thus the effect of broadening of the beam has no impact on the functioning of the refractometer.

In the context of the refractometer 1100 (conduit with circular cross section) according to the aforementioned first embodiment, the broadening of the beam by prism effect of the beam is of the same order as in the case of the refractometers 1200 and 1300, and therefore negligible.

Figure 2:
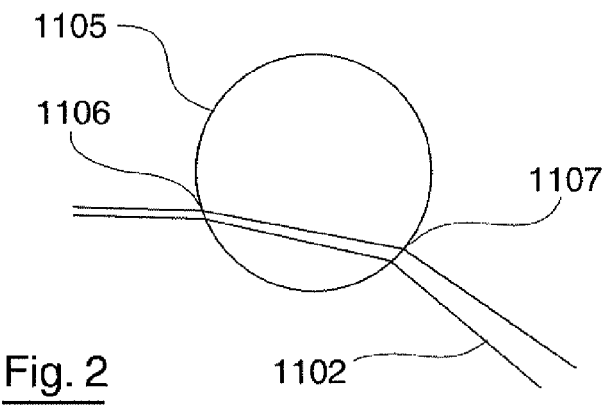
FIG. 2 illustrates the broadening of the laser beam due to the two curved dioptres at the interfaces between global optical unit and conduit and conduit and global optical unit in the refractometer according to the first embodiment of the invention described in relation to FIG. 1.

However, to this there is added the power of the cylindrical optics created by the two curved dioptres (corresponding to the interfaces between global optical unit and conduit 1106 and conduit and global optical unit 1107). As illustrated by FIG. 2, this results in a broadening of the laser beam 1102.

The angular broadening is around 2.5°, and thus, without compensation for this cylindrical effect, the spot of the laser beam 1102 designed to have a diameter of 200 m at the position sensor 1109 broadens by 1.4 mm. This broadening of the laser spot causes the resolution of the refractometer to fall. Consequently the refractometer cannot function without compensation.

The compensation for the cylindrical effect consists either of taking account in the optical path of the focal distance of the divergent cylindrical optics (which is substantially equal to 25 mm) or eliminating the cylindrical effect by bonding a window with parallel faces to each of the global optical unit/conduit 1106 and conduit/global optical unit 1107 interfaces. This solution make it possible to substantially regain the configuration of the second or third embodiments of the invention (invariance of the angle of incidence) while keeping the cylindrical geometry of the conduit.

They are obvious a laser spot size on the position sensor, which diameter of the collar φ is understood between 200 Mm and 1 mm, Mm necessary. For example φ=200 Mm is chosen.

Figure 3:
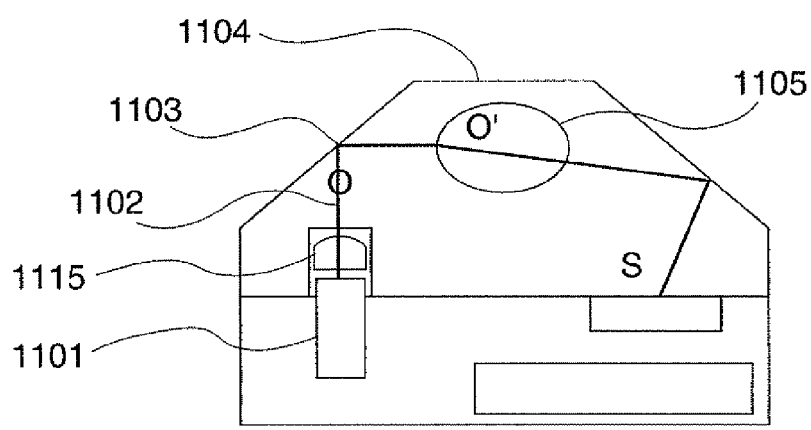
FIG. 3 illustrates the embedding of the laser diode in the glass of the global optical unit of the refractometer in order to reduce the optical path travelled by the laser beam.

The length of the optical path travelled by the laser beam 1102 is equal to a few tens of mm because of the dimensions of the global optical unit; however, it can be reduced by integrating the laser diode and its focusing optics 1115 in the global optical unit itself (as illustrated by FIG. 3). The divergence of the laser beam 1102 in the glass global optical unit (with an index of approximately 1.5) is $4\lambda/\pi\phi n=4$ mrad, where λ is the wavelength of the laser.

Figure 4:
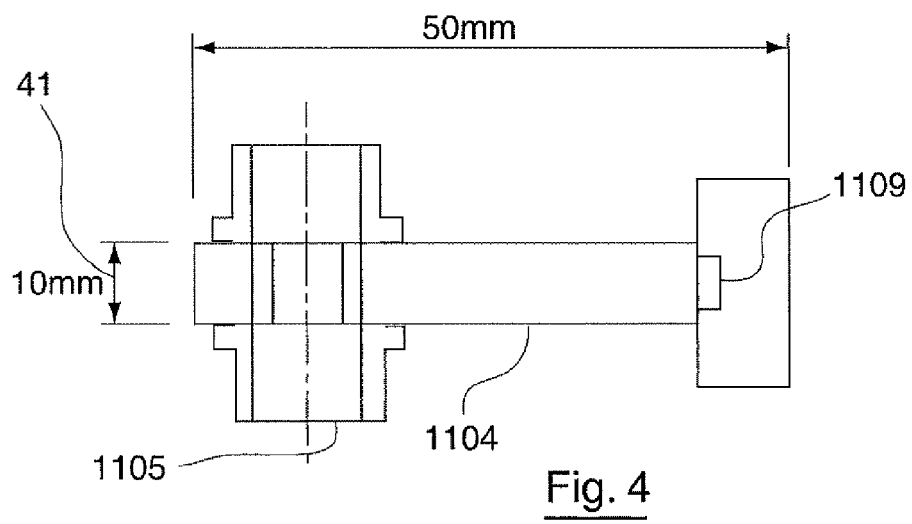
FIG. 4 presents a diagram of the refractometer according to the first embodiment of the invention in its longitudinal section.

FIG. 4 presents a diagram of the refractometer 1100 in its longitudinal section according to the first embodiment of the invention. The thickness 41 of the refractometer 100 at the global optical unit 1104 is between 10 and 20 mm. This constitutes an optimum between rigidity and sufficient thermal response.

The conduit is preferably produced from a non-oxidizable metal (for example from an Fe—Ni—Cr alloy or an anodized aluminum) that firstly optimizes the thermal response time of the refractometer and secondly makes it possible to adapt means for limiting the effects of fouling of marine origin, for example by means of TBT (tributyltin) pellets. It can also be noted that the choice of an effective cross section of the conduit substantially equal to 1 cm is compatible with the fixing of TBT pellets.

The main elements constituting the refractometer 1100 according to the first embodiment of the invention will be presented in more detail below.

The position sensor 1109 is for example a PSD marketed by the company Hamamatsu under the reference S4584-06. It is sensitive in the red range for wavelengths around 635 nm and is also sensitive for wavelengths greater than 800 nm. It has a maximum resolution of 0.1 μm (which is negligible when compared with the diameter of the laser spot) and a useful length at 2.5 mm and cooperates with an electronic circuit referenced C3683-01.

This position sensor 1109 has a good resolution, around 0.3 μm, with a relatively large positioning tolerance. These characteristics of the position sensor make it possible to envisage the use of an effective spot size of between 200 μm and 1 mm. It is shown that the quality of the beam has little effect on the result of the measurement. In addition, only the longitudinal direction is important, which allows the use of an elliptically shaped laser beam with the advantages that result therefrom for the optical mounting (in particular the simplification of the focusing optics, the fact that there is no longer any need for focusing optics except in one direction, and the fact that a low optical power is sufficient).

The laser diode 1101 is for example a collimated laser diode marketed by the company Photonic under the reference 301-P. It emits a laser beam with a wavelength of 635 nm, a power of approximately 0.9 mW, a beam size of approximately 1.8 mm×1.8 mm, a maximum divergence in air of 6 mrd and a collimated beam diameter of 8 mm.

A detailed diagram of the global optical unit 1104 of the refractometer 1100 according to the first embodiment of the invention is presented in relation to FIG. 5.

The global optical unit consists of first 11041 and second 11042 independent optical units formed from transparent materials. The first optical unit 11041 is an emission optical unit to which the laser diode 1101 and the focusing optics 1115 are secured (for example by adhesive bonding). The PSD position sensor 1109 is secured (for example by adhesive bonding) to the second optical unit 11042, substantially symmetrical with the first optical unit 11041.

The first 11041 and second 11042 optical units form a V between them in order to accept the cylindrically shaped conduit 1105 and first 11051 and second 11052 prismatic windows situated respectively between the first optical unit 11041 and the conduit 1105 and between the conduit 1105 and the second optical unit 11042. These windows make it possible to dispense with the broadening of the laser beam due to the cylindrical effect (generated by the curved dioptres of the interfaces 1106, 1107) as explained previously and to keep a constant angle of incidence.

It can be remarked that, in the case of the second and third embodiments of the invention, the first 11041 and second 11042 optical units accept respectively the conduit 1205 with a hexagonal cross section (or more generally polygonal) and the conduit 1305 with a prismatic cross section but without windows being used.

The assembly consisting of conduit 1105 and windows 11051, 11052 is kept in permanent abutment on the V of the first 11041 and second 11042 optical units by a return spring 11053.

Preferentially (but not obligatorily), transparent materials having thermo-optical coefficients that are opposite and equal in absolute value are chosen for the materials of the first 11041 and the second 11042 optical units in order to make the optical path travelled by the laser beam 1102 insensitive to variations in temperature (as explained below). Thus the variations as a function of temperature in the optical path followed by the laser beam in the first unit are compensated for by the variations as a function of temperature in the optical path travelled by the laser beam in the second unit.

It is possible for example to choose to produce the first optical unit 11041 from glass, which has its index increased with temperature, and the second optical unit 11042 from an adapted polymer that has its index decreased with temperature. The choice of the polymer must be such that the variations in the optical path in the first optical unit 11041 compensate for the variations in the optical path in the second optical unit 11042.

It is possible for example to produce the optical units from materials such as:

N-K5
N-F2
N-BAF51
N-LF5
N-SF5
N-SK10
N-BK7
N-LLF1

Appendix 1 presents a table presenting the characteristics (index, variation in the index as a function of temperature, the coefficient of absorption over a temperature range from −30° C. to 70° C. and density) of the first six aforementioned materials. These materials are able to be used without compensation for variations in their indices due to the variations in temperature because of their low thermo-optical coefficients.

Appendix 2 presents a table presenting the characteristics (index, variation in the index as a function of temperature, the coefficient of absorption over a temperature range from −30° C. to 70° C. and density) of the last two aforementioned materials. These materials constitute an example of a pair of materials having thermo-optical coefficients that are very close in absolute value and of opposite signs.

An explanation is given below of how the refractometers according to an embodiment of the invention have independence with respect to variations in temperature and pressure.

The variation in pressure and temperature during the lowering of a probe comprising a salinity sensor based on a refractometer according to an embodiment of the invention may cause a modification in the characteristics of the optical paths (which depend on pressure and temperature) and the indices (which depend essentially on temperature).

These two effects have an impact on the measurement of the refractive index of sea water because they result in a translation and/or broadening (over an acceptable broadening range) of the size of the spot on the PSD position sensor.

These two effects do not however act in the same way and at the same time. This is because it can in particular be assumed that the pressure is exerted only on the conduit (the first and second optical units being packaged in a satisfactory manner, they do not suffer the impact of pressure).

Over a temperature range extending from 0° C. to 35° C., a variation in the index of the first and second optical units can be observed as a function of the temperature of the refractometer. However, the effect of the temperature is not immediate and depends on the thermal gradient of the optical unit. In addition it does not affect these measurements at the time when it is being taken.

Over a pressure range extending from 0 to 200 bar, an expansion of the materials as a function of pressure is observed. The effect of the pressure is immediate and must be considered.

The insensitivity of the refractometers according to an embodiment of the invention to the effect of pressure (in particular with regard to the conduit) is explained below.

The pressure is exerted only inside the conduit and results in increasing the diameter of the conduit.

In the case of the conduit with a hexagonal or prismatic cross section (the refractometer according to the second and third embodiments of the invention), the expansion of the conduit does not modify the angle of incidence of the laser beam on the conduit and therefore does not interfere with the functioning of the refractometer.

In the case of the conduit with a circular cross section (the refractometer according to the first embodiment of the invention), the expansion of the conduit also does not modify the angle of incidence of the laser beam on the conduit because the latter is provided with two windows in abutment on the 60° V formed by the first and second optical units (as explained above in relation to FIG. 5).

This is because, during expansion (due to an increase in pressure), the two windows will be shifted without changing either the angle of incidence or the optical path. The conduit is held in abutment on the V for example by virtue of the spring 11053.

The insensitivity of the refractometers according to an embodiment of the invention to the effects of temperature (in particular with regard to the optical units) is explained below.

Three solutions according to embodiments of the invention (which may be combined) for making the refractometers according to the invention insensitive to variations in temperature can mainly be envisaged.

The first solution consists of measuring the temperature variation of the optical units by means of one or more temperature sensors and to make the corrections off line on the translation of the spot.

This temperature sensor or sensors must preferentially be incorporated in at least one of the optical units so as to measure precisely the change in temperature gradient. The correction is then of a software nature.

The temperature variations result in a variation in the optical path travelled in the first and second optical units due to a variation in the indices of the first and second optical units.

The second solution allowing automatic compensation for the effects of the temperature is described below.

As indicated above in relation to FIG. 5, in order to obtain insensitivity to temperature variations, it is possible to use first and second optical units formed from two transparent materials having thermo-optical coefficients equal in absolute value and opposite. It is possible for example to use a glass for the first optical unit and a polymer for the second.

This is because, if the first and second units are produced from glass, the deviation d, given by the formula: $d=2.(r-i)$, where r is the angle of refraction and i the angle of incidence, increases with temperature because r increases with temperature (because the index of the glass increases with temperature). Thus it is possible to find the initial deviation (before the variation in temperature) by increasing i, for example by replacing the second glass unit with a second polymer unit whose index decreases as a function of temperature and where the amplitude of the variation is as close as possible to that of glass.

The third solution allowing automatic compensation for the effects of temperature is described below.

According to an embodiment of the invention, in order to effect the aforementioned automatic compensation for the variations in indices of the first and second optical units, it is possible for example to compensate for the movement of the spot on the PSD position sensor with a reverse movement of the sensor itself.

Figure 6:
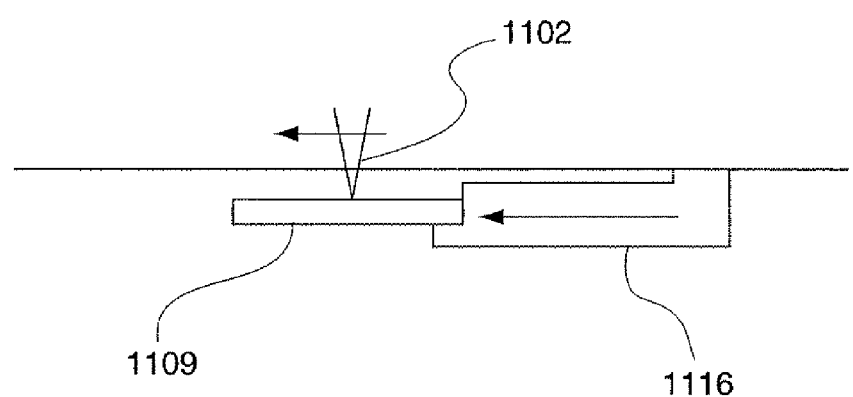
FIG. 6 illustrates the use of a support in the refractometer according to the first embodiment of the invention, the thermal expansion of which makes it possible to achieve an automatic compensation for the thermal dependency of the index of the optical units.

To do this (as illustrated by FIG. 6 in the case of the refractometer according to the first embodiment of the invention), it is possible to secure the PSD position sensor to a support 1116 produced from a material whose coefficient of differential expansion with respect to that of the piece on which it is disposed makes it possible, within the temperature range extending from 0° C. to 35° C., to move the PSD position sensor by approximately 1 µm. The expansion of the support must be chosen so as to compensate for the movement of the laser spot on the position sensor.

It is necessary for the expansion of the support to be slaved to the variation in the optical unit, which assumes a low thermal inertia between the conduit and the support of the PSD. This inertia can be reduced by a cladding of the assembly in a material identical to that of the conduit, offering good thermal conduction (for example a non-oxidisable metal). In order to further reduce this inertia, the first and second optical units made from transparent materials can be hollowed out outside the optical path travelled by the laser beam. The recess or recesses thus obtained can receive thermally conductive materials in order to reduce the thermal inertia of said unit or units.

For example, if the piece on which the support of the PSD position sensor rests is produced from steel (steel has a coefficient of thermal expansion of $dL/dT=5.10^{-7}$ m/K) and if the support carrying the PSD position sensor is made from aluminum (aluminum has a coefficient of thermal expansion of $dL/dT=5.10^{-6}$ m/K), over the aforementioned range of temperatures extending over 20° C., the differential is $0.9\times10^{-6}\times 20=18.10^{-6}$. Therefore, in order to extend by 0.5 µm and to compensate for the aforementioned movement dP of the laser spot, the aluminum piece must measure $L=2.8$ cm. The phenomenon is reversible without hysteresis and linear over the temperature range.

It is necessary for this variation to follow the variations of the optical units, for this purpose and in order to avoid any thermal gradients between the optical units and the positions sensor. To do this, a first technique according to an embodiment of the invention consists of putting part of the expansible support to which the PSD position sensor is slaved in contact with the water. A second technique according to an embodiment of the invention consists of expanding the support according to a temperature measurement made on the optical units themselves.

Thus, to summarize, there exist three main solutions to make the refractometers or salinity sensors according to embodiments of the invention insensitive to the effects of the temperature variations.

The first consists of the use of optical units having thermo-optical coefficients that compensate for each other. This solution leads to the obtaining of low-cost salinity sensors, which is ideal for producing such sensors intended to be discarded at sea.

These second consists of using a software off-line correction.

The third consists of using an expansible support for the position sensor.

These second and third solutions make it possible to obtain high-quality salinity sensors, the optical units of which can be produced from any materials.

The first and second optical units can be reconfigured. It is possible in fact to arrange them in various ways around the conduit.

Figure 7A:
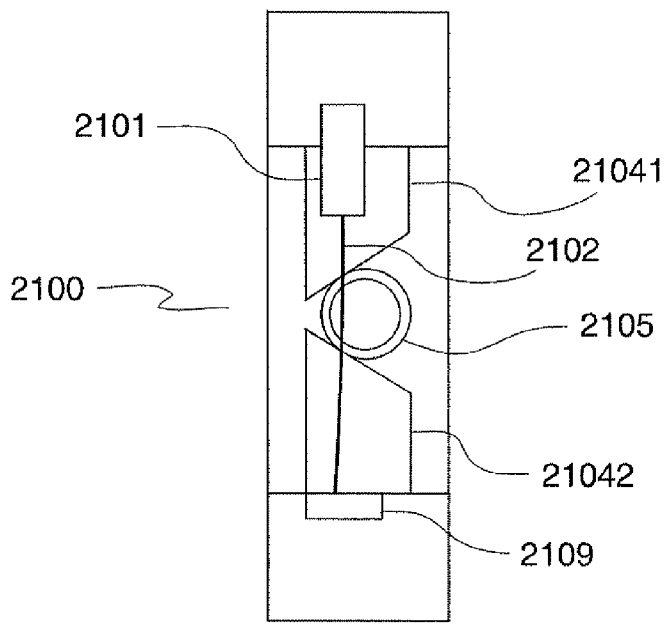
FIGS. 7A-7C are a front view (FIG. 7A), a side view (FIG. 7B) and a cross section along an axis XX' (FIG. 7C) of a refractometer according to a second implementation of the invention.
Figure 7B:
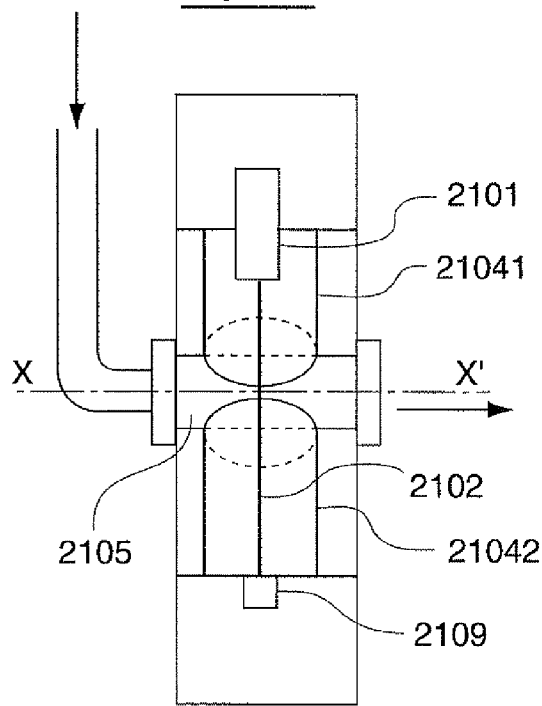
Figure 7C:
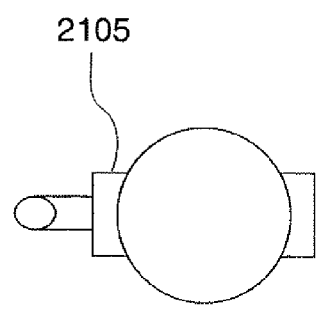

There are presented, in relation to FIGS. 7A to 7C, a front view (FIG. 7A), a side view (FIG. 7B) and a cross section along an axis X-X' (FIG. 7C) of a refractometer 2100 according to a second implementation of the invention.

The refractometer 2100 according to the second implementation of the invention is distinguished from the refractometers 1100, 1200, 1300 according to the first implementation of the invention essentially through the fact that the first 21041 and second 21042 optical units are not disposed close to each other (as in the refractometers 1100, 1200, 1300) but are substantially aligned on each side of the conduit 2105.

The conduit 2105 has a circular cross section; however, according to non-illustrated variants according to this second implementation, other conduits with a hexagonal or prismatic cross section or with a cross section of any other shape can be used.

In addition, the laser beam 2102 is no longer reflected on sides of the optical units during its travel as far as the position sensor 2109.

The two arrows disposed on FIG. 7B indicate the direction of flow of the sea water in the conduit 2105.

Figure 8:
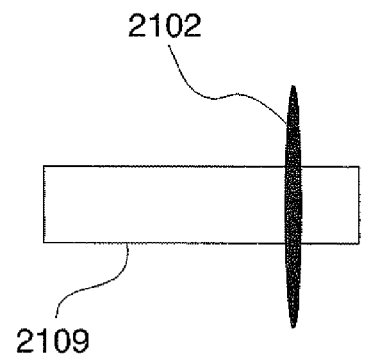
FIG. 8 illustrates the focusing of the elliptical laser beam on the position sensor in the context of the refractometer according to the second implementation of the invention.

Focusing optics (not shown) for the laser beam 2102 are also used in this refractometer 2100. FIG. 8 illustrates the focusing of the laser beam 2102, which is for example elliptical, on the PSD position sensor 2109.

Naturally the spot of the laser beam 2102 as well as the spots of the laser beams of the refractometers according to the first implementation of the invention may be circular or elliptical or have any other shape.

The refractometer 2100 (or the salinity sensor comprising the refractometer 2100) offers a reduced size compared with the configuration of the refractometer 1100, 1200, 1300 according to the first implementation of the invention and can therefore be inserted in launch tubes to aeronautical standards.

Naturally the optical units can be disposed according to other orientations around the conduit.

The aforementioned implementations and embodiments can be combined.

Naturally the invention is not limited to the example embodiments mentioned above.

In particular a person skilled in the art can make any variation in the choice of materials constituting the optical units, the position sensor support, the piece on which the position sensor support rests, the conduit, or any other part of the salinity sensor.

The invention obviously applies also in the context of other types of conduit cross sections and moreover it is possible to use, in the refractometers according to an embodiment of the present invention, conduits having cross sections variable according to the position on the conduit.

In at least one embodiment, the refractometer produces a salinity sensor that is insensitive to the variations in temperature and pressure that it undergoes.

In at least one embodiment, the refractometer has a resolution of at least $10^{-6}$.

At least one embodiment produces such a salinity sensor that is particularly adapted to measurements where it is immersed and has great resistance to fouling or organic deposition of all kinds.

At least one embodiment produces such a salinity sensor that is compact and of low cost.

Although the present disclosure has been described with reference to one or more examples, workers skilled in the art will recognize that changes may be made in form and detail without departing from the scope of the disclosure and/or the appended claims.

APPENDIX 1

| Material | Index | dn/dT (K$^{-1}$) | Alpha (cm$^{-1}$) | Density (USI) |
|---|---|---|---|---|
| N-K5 | 1.52249 | $-4.13 \times 10^{-7}$ | 8.2 | 2.59 |
| N-F2 | 1.62005 | $4.62 \times 10^{-7}$ | 7.84 | 2.65 |
| N-BAF51 | 1.65224 | $-2.84 \times 10^{-7}$ | 8.37 | 3.33 |
| N-LF5 | 1.58144 | $1.75 \times 10^{-7}$ | 8 | 2.57 |
| N-SF5 | 1.67271 | $-2.51 \times 10^{-7}$ | 7.94 | 2.86 |
| N-SK10 | 1.62278 | $5.05 \times 10^{-7}$ | 6.83 | 3.66 |

APPENDIX 2

| Material | Index | dn/dT (K$^{-1}$) | Alpha (cm$^{-1}$) | Density (USI) |
|---|---|---|---|---|
| N-BK7 | 1.5168 | $1.86 \times 10^{-6}$ | 7.1 | 2.51 |
| N-LLF1 | 1.54814 | $-1.85 \times 10^{-6}$ | 7.97 | 2.49 |

The invention claimed is:

1. Optical refractometer for measuring the refractive index of a liquid, wherein the refractometer comprises:
   a first optical unit comprising a first transparent material to which a light source is secured, and
   a second optical unit comprising a second transparent material to which an optical position sensor, capable of measuring deviation of a light beam from the light source, is secured, said optical units being disposed on each side of a conduit in which said liquid flows, wherein the first and second materials have thermo-optical coefficients that are opposite and substantially equal in absolute value.

2. Refractometer according to claim 1, wherein the liquid comprises sea water and the refractometer is able to function when the refractometer is immersed.

3. Refractometer according to claim 1, wherein said light source comprises a laser source cooperating with focussing optics focussing the laser beam on the position sensor.

4. Refractometer according to claim 3, the laser beam has a spot size focussed on the position sensor between 200 µm and 1 mm.

5. Refractometer according to claim 3, wherein the focussing optics is disposed close to the laser source.

6. Refractometer according to claim 3, wherein the laser source emits in the visible range.

7. Refractometer according to claim 1, wherein the first and second units are disposed close to each other and form a V for housing the conduit, and the first unit comprises a first side comprising a first mirror and the second unit comprises a second side comprising a second mirror, so that the laser beam is reflected on the first mirror, passes through the conduit and is reflected on the second minor.

8. Refractometer according to claim 1, wherein the laser beam has an angle of refraction in the liquid of the conduit between 29° and 31°.

9. Refractometer according to claim 7, wherein the refractometer further comprises return means for holding the conduit against the V.

10. Refractometer according to claim 1, wherein the first and second optical units are substantially aligned on each side of the conduit.

11. Refractometer according to claim 1, wherein the conduit has a substantially circular cross section at a point where the laser beam passes through the conduit and first and second windows are provided respectively between the first unit and the conduit and between the conduit and the second unit.

12. Refractometer according to claim 1, wherein the conduit has a substantially polygonal cross section at a point where the laser beam passes through the conduit.

13. Refractometer according to claim 12, wherein the cross section of the conduit is substantially hexagonal at the point where the laser beam passes through the conduit.

14. Refractometer according to claim 12, the cross section of the conduit is substantially prismatic at the point where the laser beam passes through the conduit.

15. Refractometer according to claim 1, wherein the first and second transparent materials are chosen from all materials comprising:
   N-K5
   N-F2
   N-BAF51
   N-LF5
   N-SF5
   N-SK10.

16. Refractometer according to claim 15, wherein the first and second materials are respectively N-BK7 and N-LLF1 or N-K5 and N-SK10.

17. Refractometer according to claim 15, wherein at least one of said first and second units are at least partially hollowed out, the hollow or hollows being intended to receive thermally conductive materials in order to reduce the thermal inertia of said unit or units.

18. Refractometer according to claim 1, wherein the refractometer comprises a temperature sensor and electronic unit, which measures variation in temperature of at least one of the optical units and derives therefrom salinity or refractive index of the liquid.

19. Refractometer according to claim 1, wherein the position sensor is secured to a support having dimensions that vary according to temperature so as to at least compensate for a shift of an optical beam, emitted from the light source, with respect to said position sensor as a function of temperature.

20. Refractometer according to claim 19, wherein the support is produced from a thermally conductive material and at least part of the support is in thermal contact with the liquid to be measured.

21. Refractometer according to claim 19, wherein the support is produced from thermally conductive material and the variation in dimensions is, by virtue of processing means, slaved to at least one temperature sensor mounted close to at least one of said optical units.

22. A salinity sensor comprising:
   an optical refractometer for measuring a refractive index of a liquid, wherein the refractometer comprises:
      a first optical unit comprising a first transparent material to which a light source is secured, and
      a second optical unit comprising a second transparent material to which a position sensor is secured, said optical units being disposed on each side of a conduit in which said liquid flows, wherein the first and second materials have thermo-optical coefficients that are opposite and substantially equal in absolute value.

* * * * *